(12) United States Patent
Veenstra

(10) Patent No.: US 7,678,814 B2
(45) Date of Patent: Mar. 16, 2010

(54) AROYL-PIPERIDINE DERIVATIVES

(75) Inventor: Siem Jacob Veenstra, Lörrach (DE)

(73) Assignee: Novartis AG, Basel (CH)

( * ) Notice: Subject to any disclaimer, the term of this patent is extended or adjusted under 35 U.S.C. 154(b) by 780 days.

(21) Appl. No.: 10/527,518

(22) PCT Filed: Sep. 9, 2003

(86) PCT No.: PCT/EP03/10007

§ 371 (c)(1),
(2), (4) Date: Sep. 26, 2005

(87) PCT Pub. No.: WO2004/024714

PCT Pub. Date: Mar. 25, 2004

(65) Prior Publication Data

US 2006/0135558 A1    Jun. 22, 2006

(30) Foreign Application Priority Data

Sep. 10, 2002 (GB) ................. 0220953.4

(51) Int. Cl.
*C07D 215/38* (2006.01)
*A61K 31/44* (2006.01)

(52) U.S. Cl. ............ 514/312; 514/313; 514/314; 546/157; 546/169

(58) Field of Classification Search ............ 546/157, 546/169; 514/312, 313, 314
See application file for complete search history.

(56) References Cited

U.S. PATENT DOCUMENTS 5,310,743 A * 5/1994 Schilling et al. ............ 514/311
5,965,562 A   10/1999 Ofner et al.

FOREIGN PATENT DOCUMENTS

| EP | 0 707 006 | 4/1996 |
|---|---|---|
| EP | 0 739 892 | 10/1996 |
| WO | WO 97 45119 | 12/1997 |
| WO | WO 99 61025 | 12/1999 |
| WO | WO 00/10545 | 3/2000 |

OTHER PUBLICATIONS

Xing Qiyi, Fundamental Organic Chemistry, 2nd Edition, June 1994, p. 925 (Also identified as Reference 2 - English translation of relevant Chinese-language portion).
Silvio Ofner et al., Bioorganic & Medicinal Chem. Letters, vol. 6, No. 14, pp. 1623-1628, 1996.

* cited by examiner

*Primary Examiner*—D. Margaret Seaman
(74) *Attorney, Agent, or Firm*—Montgomery, McCrocken, Walker & Rhoads, LLP; Robert R. Axenfeld; Kristin M. Nevins

(57) ABSTRACT

The invention relates to novel N-(3,5-bis-trifluoromethyl-benzoyl)-2-benzyl-4-(quinoloy-lamino)-piperidines of the formula . . . wherein Y and R each are as defined above and the ring A is unsubstituted or mono- or polysubstituted by substituents selected from the group consisting of lower alkyl, lower alkoxy, halogen, nitro and trifluoromethyl; and the salts thereof, to the use thereof, to processes for the preparation thereof and to pharmaceutical compositions comprising a compound according to the invention.

7 Claims, No Drawings

AROYL-PIPERIDINE DERIVATIVES

The invention relates to novel N-(3,5-bis-trifluoromethyl-benzoyl)-2-benzyl-4-(quinoloylamino)-piperidines of the formula

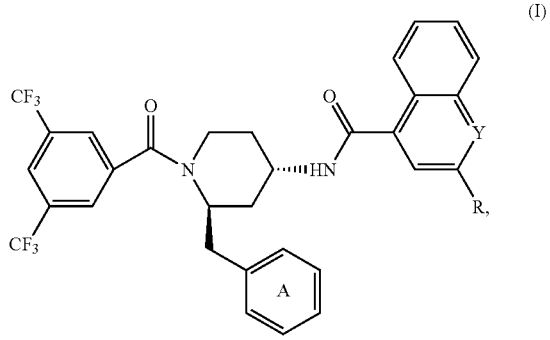

(I)

wherein Y is =N— or =N(O)—, R is OH when Y is =N— and R is H when Y is =N(O)— and the ring A is unsubstituted or mono- or poly-substituted by substituents selected from the group consisting of lower alkyl, lower alkoxy, halogen, nitro and trifluoromethyl, provided that when R is OH and Y is =N— the ring A is not unsubstituted; to the use thereof; to processes for the preparation thereof and to pharmaceutical compositions comprising a compound according to the invention.

Since the compounds according to the invention have at least two optically active carbon atoms they may accordingly be present in the form of stereoisomers, stereoisomeric mixtures and in the form of the (substantially) pure diastereoisomers. The present invention relates also to corresponding stereoisomers.

Preference is given to compounds of formula I wherein the ring A is substituted.

Unless otherwise defined, the general terms used hereinbefore and hereinafter have the meanings given below.

The term "lower" denotes that groups and compounds so defined each have from 1 up to and including 7, preferably from 1 up to and including 4, carbon atoms.

Lower alkyl is, for example, methyl, ethyl, n-propyl, isopropyl, n-butyl, isobutyl, sec-butyl, tert-butyl or a corresponding pentyl, hexyl or heptyl radical. $C_1$-$C_4$alkyl is preferred.

Lower alkoxy is, for example, methoxy, ethoxy, n-propyloxy, isopropyloxy, n-butyloxy, iso-butyloxy, sec-butyloxy, tert-butyloxy or a corresponding pentyloxy, hexyloxy or heptyloxy radical $C_1$-$C_4$alkoxy is preferred.

Halogen is especially halogen having an atomic number of up to and including 35, i.e. fluorine, chlorine or bromine, and also includes iodine. Chlorine is preferred.

Substance P is a naturally occurring undecapeptide of the tachykinin family. It is produced in mammals and acts pharmacologically as a neuropeptide. Substance P plays an important role in various disorders, for example in the case of painful conditions, in migraines and in certain disorders of the central nervous system, such as anxiety states, vomiting, schizophrenia and depression, and in certain motor disorders, such as Parkinson's disease, but also in inflammatory diseases, such as rheumatoid arthritis iritis and conjunctivitis, in diseases of the respiratory organs, such as asthma and chronic bronchitis, in diseases of the gastrointestinal system, such as ulcerative colitis and Crohn's disease, and in hypertension.

A great deal of work is being done to advance the development of the field of substance-P-antagonists and, for example, to find suitable substance-P-antagonists having a broad spectrum of action that exhibit outstanding in vivo activity and increased bioavailability as well as improved chemical stability.

Extensive pharmacological studies have shown that the compounds according to the invention antagonise substance P to an especially preferred extent and thus inhibit the symptoms induced by substance P.

The substance-P-antagonising effects can be demonstrated—as shown below—using test methods known to the person skilled in the art. Such effects are observed both in vitro and in vivo. For example, the substance-P-induced formation of phosphoinositol in human astrocytoma cells is antagonised in vitro by the compounds of formula I and IA. $IC_{50}$ values of from approximately 1 nmol are found. A suitable test model for the detection of that inhibition is, for example, the test method of Lee, C. M. et al., as described in J. Neurochem. 59, 406-414 (1992).

In addition, the binding of $^3$H-substance P to bovine retina in the radio receptor assay according to H. Bittiger, Ciba Foundation Symposium 91, 196-199 (1982) is inhibited with $IC_{50}$ values of from approximately 1 nmol. For example, the following in vitro values of about 10 nM were obtained for the target compounds of Examples 1 and 2.

A change in behaviour is produced in gerbils by i.c.v. administration of substance P methyl ester. That effect can be inhibited in vivo after peroral administration of compounds of formulae I and IA and the salts thereof. A. Vassout et al. which was presented at the "Substance P and Related Peptides: Cellular and Molecular Physiology" Congress in Worchester, Mass., in 1990. In that method, $ED_{50}$ values of from approximately 0.1 mg/kg p.o. are obtained, demonstrating their usefulness in the treatment of disorders of the central nervous system.

In vivo, using the experimental procedure of Lundberg et al., Proc. Nat. Acad. Sci. (USA) 80, 1120-1124, the compounds of formulae I and IA and the salts thereof inhibit vagally induced bronchospasms in guinea pigs at a dose of from approximately 1.0 mg/kg i.v., which demonstrates their suitability for the treatment of asthma.

The substance-P-antagonists of formulae I and IA prepared in accordance with the invention and the pharmaceutically acceptable salts thereof are accordingly outstandingly suitable for the therapeutic treatment of the pathological symptoms listed hereinbefore.

The invention relates also to a method of treating disorders induced by substance P by the administration of a therapeutically effective amount of a compound of formula I or IA.

The present invention relates also to the use of a compound of formula I or IA in the preparation of medicaments for the treatment of disorders induced by substance P.

The invention relates also to the use of compounds of formula I or IA as biochemical tools, for example for the identification and, possibly, the profiling of further potent substance-P-antagonists.

The invention relates especially to compounds of formula IA

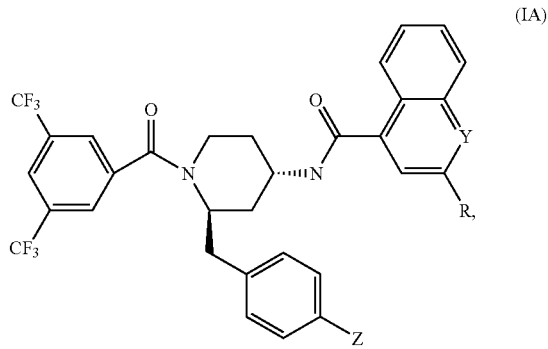

(IA)

wherein Y and R are as defined above and Z is hydrogen, halogen or nitro, provided that when R is OH and Y is =N—Z is not H.

The invention relates above all to compounds of formula IA wherein Y and R are defined above and Z is halogen, such as chlorine.

The invention relates specifically to the compounds of formula I mentioned in the Examples.

The invention relates also to processes for the preparation of the compounds according to the invention. Those processes comprise oxidising a compound of formula II

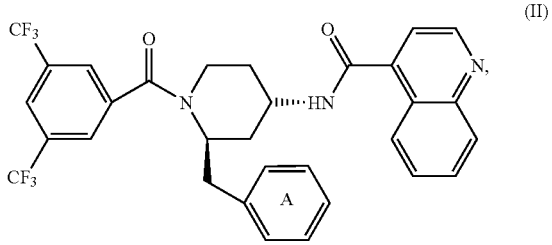

and, if desired, separating a mixture of isomers obtainable by the process and isolating the desired isomer.

The compound of formula II may be oxidised to give a compound of formula I; for instance, with 3-chloroperbenzoic acid at room temperature.

Alternatively compounds of formula I in which R is OH and Y is =N— may be prepared by linking of the corresponding [(2R,4S)-4-Amino-2-(4-benzyl-piperidin-1-yl]-(3,5-bis trifluormethyl-phenyl)-methanone with 2-hydroxyquinoline-4-carboxylic acid; for instance as hereinafter described in Example 2.

The invention is illustrated especially by the Examples and relates also to the novel compounds mentioned in the Examples and to the processes for the preparation thereof.

The compounds of formula I and IA, may also be obtained in the form of hydrates or may include the solvent used for crystallisation.

Resulting mixtures of diastereoisomers and mixtures of racemates can be separated in known manner into the pure diastereoisomers or racemates on the basis of the physicochemical differences between the constituents, for example by chromatography and/or fractional crystallisation.

Resulting racemates can also be separated into the optical antipodes by known methods, for example by recrystallisation from an optically active solvent, with the aid of microorganisms or by reaction of the resulting diastereoisomeric mixture or racemate with an optically active auxiliary compound, for example according to the acidic, basic or functionally modifiable groups present in compounds of formulae I and IA with an optically active acid, base or an optically active alcohol, into mixtures of diastereoisomeric salts or functional derivatives, such as esters, and separation thereof into the diastereoisomers from which the desired enantiomer can be freed in the appropriate customary manner. Examples of suitable bases, acids and alcohols are optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluyltartaric acid, D- or L-malic acid, D- or L-mandelic acid, or D- or L-camphorsulfonic acid, or optically active alcohols, such as borneol or D- or L-(1-phenyl)ethanol.

The novel compounds of formulae I and IA can be used, for example, in the form of pharmaceutical compositions that comprise a therapeutically effective amount of the active ingredient, optionally together with inorganic or organic, solid or liquid, pharmaceutically acceptable carriers that are suitable for enteral, for example oral, or parenteral administration. There are used, for example, tablets or gelatin capsules that comprise the active ingredient together with diluents, for example lactose, dextrose, saccharose, mannitol, sorbitol, cellulose and/or lubricants, for example silica, talc, stearic acid or salts thereof, such as magnesium or calcium stearate, and/or polyethylene glycol. Tablets can also comprise binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colourings, flavourings and sweeteners. The novel compounds of formulae I and IA can also be used in the form of parenterally administrable compositions or in the form of infusion solutions. Such solutions are preferably isotonic aqueous solutions or suspensions which, for example in the case of lyophilised compositions that comprise the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions in question, which, if desired, may comprise further pharmacologically active substances, are prepared in a manner known per se, for example by means of conventional mixing, granulating, confectioning, dissolving or lyophilising processes, and comprise from approximately 0.1% to 100%, especially from approximately 1% to approximately 50%, in the case of lyophilisates up to approximately 100%, active ingredient.

The invention relates also to the use of the compounds of formulae I and IA, preferably in the form of pharmaceutical compositions. The dose can depend on various factors, such as the mode of administration, species, age and/or individual condition. The daily doses to be administered are, in the case of oral administration, from approximately 0.25 to approximately 10 mg/kg, and in the case of warm-blooded animals having a body weight of approximately 70 kg, they are preferably from approximately 20 mg to approximately 500 mg.

The following Examples illustrate the invention; temperatures are given in degrees Celsius and pressures in mbar.

EXAMPLE 1

1-Oxy-quinoline-4-carboxylic acid [(2R,4S)-1-(3,5-bis-trifluoromethyl-benzoyl)-2-(4-chloro-benzyl)-piperidin-4-yl]-amide

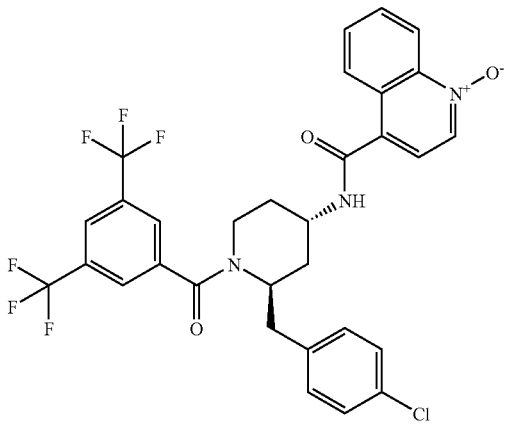

To a solution of 6.0 g (9.68 mMol) quinoline-4-carboxylic acid [(2R,4S)-1-(3,5-bis-trifluoromethyl-benzoyl)-2-(4- chloro-benzyl)-piperidin-4-yl]-amide (Synthesis described in EP 707 006 A) in 60 ml of $CH_2Cl_2$ were added 2.07 g (10.2 mMol) of 3-chloroperbenzoic acid (85%) at room temperature with stirring. After the mixture became homogeneous it was left a room temperature for 18 hrs. The mixture was washed successively with 5% aqueous $NaHSO_3$ and 10% aqueous $NaHCO3$. The organic phase was dried with $K_2CO_3$ and concentrated in vacuo. The crude product was recrystallized from $MeOH/H_2O$. Yield 4.9 g white crystals. Mp. 223-225° C.

MS(ES+): $[M+1]^+$=636 and $[M+23]^+$=658.

EXAMPLE 2

2-Hydroxy-quinoline-4-carboxylic acid [(2R,4S)-1-(3,5-bis-trifluoromethyl-benzoyl)-2-(4-chloro-benzyl)-piperidin-4-yl]-amide

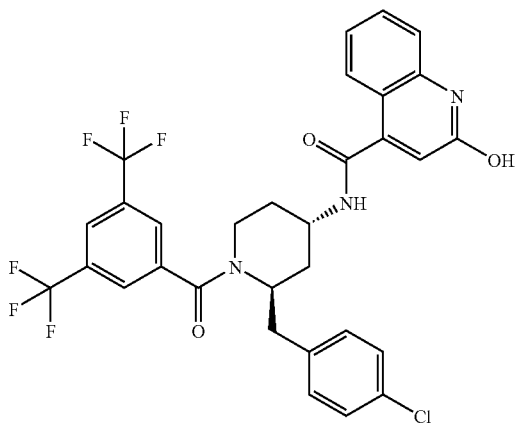

To a stirred mixture of 2.52 g (13.32 mMol) 2-hydroxyquinoline-4-carboxylic acid, 2.7 g (15.98 mMol) HOBt (80%), 3.7 ml (26.64 mMol) triethylamine and 3.8 g (18.64 mMol) DCC in 50 ml of $CH_2Cl_2$ were added at room temperature 12.3 g (13.32 mMol) [(2R,4S)-4-Amino-2-(4-chloro-benzyl)-piperidin-1-yl]-(3,5-bis-trifluoromethyl-phenyl)-methanone (synthesis described in EP 707006A). After 18 h the reaction mixture was diluted with 500 ml THF and filtered through a fritted glass funnel with suction. The filtrate was further diluted with ethyl acetate and washed three times with brine. The organic phase was dried with $Na_2SO_4$ and concentrated in vacuo. The product was purified by chromatography on silica gel using successively $EtOAc/CH_2Cl_2$ (2:1), EtOAc and EtOAc/THF (3:1) as eluents. The product was suspended in hexane and stirred at 60° C. overnight. The mixture was filtered and dried and a yield of 6.2 g of white crystals. M.p.222-224° C.

$[M+1]^+$=636 and $[M+23]^+$=658

EXAMPLE 3

Tablets, each comprising 50 mg of (2R,4S)-N-[1-(3,5-bis-trifluoromethylbenzoyl)-2-benzyl-piperidin-4-yl]quinoline-N-oxide-4-carboxamide can be prepared as follows:

Composition (10 000 Tablets)

| | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are mixed in and the mixture is compressed to form tablets, each weighing 145.0 mg and comprising 50.0 mg of active ingredient; the tablets may, if desired, be provided with breaking notches for finer adaptation of the dose.

EXAMPLE 4

Film-coated tablets, each comprising 100 mg of (2R,4S)-N-[1-(3,5-bis-trifluoromethyl-benzoyl)-2-benzyl-piperidin-4-yl]-3-hydroxy-quinoline-4-carboxamide can be prepared as follows:

Composition (For 1000 Film-Coated Tablets)

| | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 280 mg) which are then film-coated with a solution of the hydroxypropylmethylcellulose and the shellac in methylene chloride; final weight of the film-coated tablet: 283 mg.

EXAMPLE 5

Hard gelatin capsules, comprising 100 mg of active ingredient, for example (2R,4S)-N-[1-(3,5-bis-bifluoromethyl-benzoyl)-2-benzyl-piperidin-4-yl]-quinoline-N-oxide-4-carboxamide or a salt, for example the hydrochloride, thereof, can be prepared, for example, as follows:

Composition (For 1000 Capsules)

| | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 390 mg of the resulting formulation.

The invention claimed is:
1. A compound of the formula

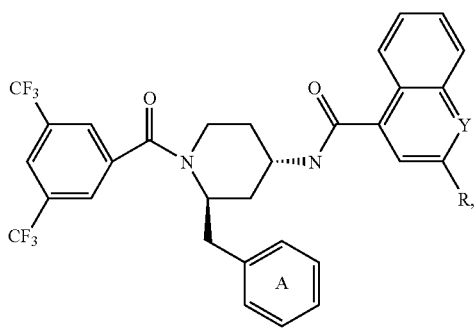

(I)

wherein Y is =N— or =N(O)—, R is OH when Y is =N— and R is H when Y is =N(O)— and the ring A is unsubstituted or mono- or poly-substituted by substituents selected from the group consisting of lower alkyl, lower alkoxy, halogen, nitro and trifluoromethyl, provided that when R is OH and Y is =N— the ring A is not unsubstituted, and pharmaceutically acceptable salts thereof.

2. A compound according to claim 1 of formula 1A

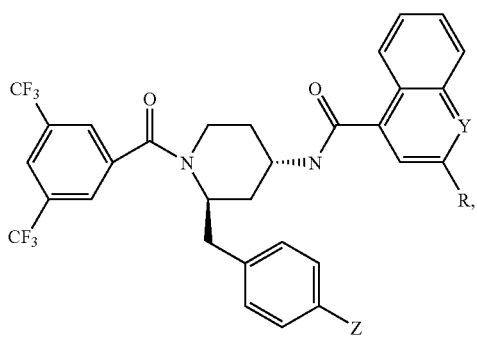

(IA)

wherein Y is =N— or =N(O)—, R is OH when Y is =N— and R is H when Y is =N(O)—, and Z is hydrogen, halogen or nitro, provided that when R is OH and Y is =N— Z is not H, and pharmaceutically acceptable salts thereof.

3. A compound according to claim 2, wherein Y is =N— or =N(O)—, R is OH when Y is =N— and R is H when Y is =N(O)—, and Z is halogen.

4. A compound selected from: 1-oxy-quinoline-4-carboxylic acid [(2R,4S)-1-(3,5-bis-trifluoromethyl-benzoyl)-2-(4-chloro-benzyl)piperidin-4-yl]-amide or a pharmaceutically acceptable salt thereof, or 2-hydroxy-quinoline-4-carboxylic acid [(2R,4S)-1-(3,5-bis-trifluoromethyl-benzoyl)-2-(4-chloro-benzyl)-piperidin-4-yl]-amide or a pharmaceutically acceptable salt thereof.

5. A method of treating a condition characterized by substance-P induction, in an animal in need thereof comprising: administering an amount of substance-P antagonist effective to inhibit the induction of substance-P, wherein the substance-P antagonist is a compound according to claim 1.

6. A pharmaceutical composition comprising a compound according to claim 1.

7. A process for the preparation of a compound of Formula I, comprising:

oxidising a compound of formula II;

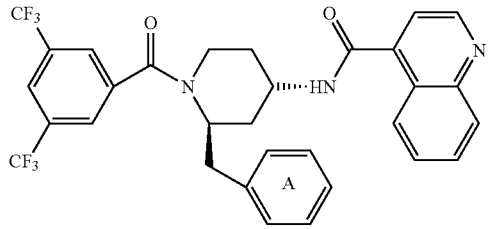

optionally separating a mixture of isomers obtainable by the process; and isolating the desired isomer of the resulting oxidized compound.

* * * * *